United States Patent
Abunassar

(10) Patent No.: US 11,701,229 B2
(45) Date of Patent: Jul. 18, 2023

(54) KIT WITH COAPTATION AID AND FIXATION SYSTEM AND METHODS FOR VALVE REPAIR

(71) Applicant: EVALVE, INC., Santa Clara, CA (US)

(72) Inventor: Chad Abunassar, San Francisco, CA (US)

(73) Assignee: EVALVE, INC., Santa Clara, CA (US)

(*) Notice: Subject to any disclaimer, the term of this patent is extended or adjusted under 35 U.S.C. 154(b) by 24 days.

(21) Appl. No.: 17/096,684

(22) Filed: Nov. 12, 2020

(65) Prior Publication Data

US 2021/0145577 A1    May 20, 2021

Related U.S. Application Data

(60) Provisional application No. 62/935,241, filed on Nov. 14, 2019.

(51) Int. Cl.
*A61F 2/24*      (2006.01)

(52) U.S. Cl.
CPC ............ *A61F 2/246* (2013.01); *A61F 2/2466* (2013.01); *A61F 2/2433* (2013.01); *A61F 2/2436* (2013.01); *A61F 2210/0004* (2013.01); *A61F 2210/0014* (2013.01); *A61F 2220/0008* (2013.01);
(Continued)

(58) Field of Classification Search
CPC .................................................... A61F 2/246
See application file for complete search history.

(56) References Cited

U.S. PATENT DOCUMENTS

| | | |
|---|---|---|
| 3,378,010 A | 4/1968 | Codling et al. |
| 3,874,388 A | 4/1975 | King et al. |
| 4,007,743 A | 2/1977 | Blake |

(Continued)

FOREIGN PATENT DOCUMENTS

| | | |
|---|---|---|
| CA | 2 296 317 C | 1/2009 |
| EP | 0 558 031 B1 | 9/1993 |

(Continued)

OTHER PUBLICATIONS

"MitraClip Transcatheter Edge-to-Edge Repair", Abbott, accessed Jul. 29, 2022. https://mitraclip.com/physician/ (Year: 2022).*

(Continued)

*Primary Examiner* — Rebecca S Preston
(74) *Attorney, Agent, or Firm* — Baker Botts L.L.P.

(57) ABSTRACT

Kit includes coaptation aid and fixation system for repair of leaflets of a heart valve. Coaptation aid includes coaptation catheter having an expandable member at a distal end thereof adapted to be introduced to a left ventricular outflow tract of a heart via a retrograde approach. Expandable member has a delivery configuration with a reduced cross-dimension and a deployed configuration with an expanded cross-dimension adapted to contact a ventricular side of a first leaflet of a heart valve and position the first leaflet generally proximate a coapting configuration with a second leaflet. Fixation system includes a delivery catheter having a distal end, and a fixation device removably coupled to the distal end of the delivery catheter and is adapted to couple the first leaflet to the second leaflet of the heart valve. Methods for fixation of native leaflets of a heart valve using a coaptation aid also disclosed.

28 Claims, 7 Drawing Sheets

(52) U.S. Cl.
CPC .............. *A61F 2250/0067* (2013.01); *A61F 2250/0096* (2013.01)

(56) References Cited

U.S. PATENT DOCUMENTS

| | | |
|---|---|---|
| 4,055,861 A | 11/1977 | Carpentier et al. |
| 4,327,736 A | 5/1982 | Inoue |
| 4,340,091 A | 7/1982 | Skelton et al. |
| 4,657,024 A | 4/1987 | Coneys |
| 4,693,248 A | 9/1987 | Failla |
| 4,716,886 A | 1/1988 | Schulman et al. |
| 4,795,458 A | 1/1989 | Regan |
| 4,809,695 A | 3/1989 | Gwathmey et al. |
| 4,930,674 A | 6/1990 | Barak |
| 5,002,562 A | 3/1991 | Oberlander |
| 5,069,679 A | 12/1991 | Taheri |
| 5,098,440 A | 3/1992 | Hillstead |
| 5,125,895 A | 6/1992 | Buchbinder et al. |
| 5,147,370 A | 9/1992 | McNamara et al. |
| 5,171,259 A | 12/1992 | Inoue |
| 5,222,963 A | 6/1993 | Brinkerhoff et al. |
| 5,271,544 A | 12/1993 | Fox et al. |
| 5,327,905 A | 7/1994 | Avitall |
| 5,330,501 A | 7/1994 | Tovey et al. |
| 5,334,217 A | 8/1994 | Das |
| 5,363,861 A | 11/1994 | Edwards et al. |
| 5,389,077 A | 2/1995 | Melinyshyn et al. |
| 5,403,326 A | 4/1995 | Harrison et al. |
| 5,425,744 A | 6/1995 | Fagan et al. |
| 5,450,860 A | 9/1995 | O'Connor |
| 5,452,837 A | 9/1995 | Williamson, IV et al. |
| 5,456,400 A | 10/1995 | Shichman et al. |
| 5,456,674 A | 10/1995 | Bos et al. |
| 5,478,353 A | 12/1995 | Yoon |
| 5,542,949 A | 8/1996 | Yoon |
| 5,562,678 A | 10/1996 | Booker |
| 5,601,224 A | 2/1997 | Bishop et al. |
| 5,601,574 A | 2/1997 | Stefanchik et al. |
| 5,607,462 A | 3/1997 | Imran |
| 5,607,471 A | 3/1997 | Seguin et al. |
| 5,609,598 A | 3/1997 | Laufer et al. |
| 5,611,794 A | 3/1997 | Sauer et al. |
| 5,636,634 A | 6/1997 | Kordis et al. |
| 5,695,504 A | 12/1997 | Gifford, III et al. |
| 5,713,911 A | 2/1998 | Racenet et al. |
| 5,716,417 A | 2/1998 | Girard et al. |
| 5,741,297 A | 4/1998 | Simon |
| 5,755,778 A | 5/1998 | Kleshinski |
| 5,782,239 A | 7/1998 | Webster, Jr. |
| 5,797,960 A | 8/1998 | Stevens et al. |
| 5,810,847 A | 9/1998 | Laufer et al. |
| 5,814,097 A | 9/1998 | Sterman et al. |
| 5,843,178 A | 12/1998 | Vanney et al. |
| 5,849,019 A | 12/1998 | Yoon |
| 5,855,601 A | 1/1999 | Bessler et al. |
| 5,976,159 A | 11/1999 | Bolduc et al. |
| 6,015,417 A | 1/2000 | Reynolds, Jr. |
| 6,048,351 A | 4/2000 | Gordon et al. |
| 6,079,414 A | 6/2000 | Roth |
| 6,117,144 A | 9/2000 | Nobles et al. |
| 6,120,496 A | 9/2000 | Whayne et al. |
| 6,149,658 A | 11/2000 | Gardiner et al. |
| 6,165,183 A | 12/2000 | Kuehn et al. |
| 6,182,664 B1 | 2/2001 | Cosgrove |
| 6,193,734 B1 | 2/2001 | Bolduc et al. |
| 6,200,315 B1 | 3/2001 | Gaiser et al. |
| 6,217,528 B1 | 4/2001 | Koblish et al. |
| 6,269,819 B1 | 8/2001 | Oz et al. |
| 6,290,674 B1 | 9/2001 | Roue et al. |
| 6,312,447 B1 | 11/2001 | Grimes |
| 6,332,880 B1 | 12/2001 | Yang et al. |
| 6,346,074 B1 | 2/2002 | Roth |
| 6,419,696 B1 | 7/2002 | Ortiz et al. |
| 6,461,366 B1 | 10/2002 | Seguin |
| 6,482,224 B1 | 11/2002 | Michler et al. |
| 6,496,420 B2 | 12/2002 | Manning |
| 6,544,215 B1 | 4/2003 | Bencini et al. |
| 6,551,303 B1 | 4/2003 | Van Tassel et al. |
| 6,575,971 B2 | 6/2003 | Hauck et al. |
| 6,599,311 B1 | 7/2003 | Biggs et al. |
| 6,626,930 B1 | 9/2003 | Allen et al. |
| 6,629,534 B1 | 10/2003 | St. Goar et al. |
| 6,669,687 B1 | 12/2003 | Saadat |
| 6,695,866 B1 | 2/2004 | Kuehn et al. |
| 6,719,767 B1 | 4/2004 | Kimblad |
| 6,752,813 B2 | 6/2004 | Goldfarb et al. |
| 6,770,083 B2 | 8/2004 | Seguin |
| 6,797,002 B2 | 9/2004 | Spence et al. |
| 6,837,867 B2 | 1/2005 | Kortelling |
| 6,855,137 B2 | 2/2005 | Bon |
| 6,875,224 B2 | 4/2005 | Grimes |
| 6,908,481 B2 | 6/2005 | Cribier |
| 6,926,730 B1 | 8/2005 | Nguyen et al. |
| 7,011,669 B2 | 3/2006 | Kimblad |
| 7,074,206 B2 | 7/2006 | Lee et al. |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,226,467 B2 | 6/2007 | Lucatero et al. |
| 7,556,632 B2 | 7/2009 | Zadno |
| 7,563,267 B2 | 7/2009 | Goldfarb et al. |
| 7,569,062 B1 | 8/2009 | Kuehn et al. |
| 7,604,646 B2 | 10/2009 | Goldfarb et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,736,388 B2 | 6/2010 | Goldfarb et al. |
| 7,811,296 B2 | 10/2010 | Goldfarb et al. |
| 7,828,766 B2 | 11/2010 | Durcan |
| 7,972,323 B1 | 7/2011 | Bencini et al. |
| 7,981,139 B2 | 7/2011 | Martin et al. |
| 8,052,638 B2 | 11/2011 | Lee et al. |
| 8,057,493 B2 | 11/2011 | Goldfarb et al. |
| 8,062,313 B2 | 11/2011 | Kimblad |
| 8,118,822 B2 | 2/2012 | Schaller et al. |
| 8,216,230 B2 | 7/2012 | Hauck et al. |
| 8,216,256 B2 | 7/2012 | Raschdorf, Jr. et al. |
| 8,303,608 B2 | 11/2012 | Goldfarb et al. |
| 8,394,055 B2 | 3/2013 | Durcan |
| 8,500,761 B2 | 8/2013 | Goldfarb et al. |
| 8,734,505 B2 | 5/2014 | Goldfarb et al. |
| 8,740,920 B2 | 6/2014 | Goldfarb et al. |
| 9,132,259 B2 | 9/2015 | Lin et al. |
| 9,510,829 B2 | 12/2016 | Goldfarb et al. |
| 10,076,415 B1 | 9/2018 | Metchik et al. |
| 10,086,175 B2 | 10/2018 | Torres et al. |
| 10,105,222 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,231,837 B1 | 3/2019 | Metchik et al. |
| 10,238,493 B1 | 3/2019 | Metchik et al. |
| 10,245,144 B1 | 4/2019 | Metchik et al. |
| D847,983 S | 5/2019 | Ho et al. |
| 10,314,586 B2 | 6/2019 | Greenberg et al. |
| 10,413,408 B2 | 9/2019 | Krone et al. |
| 10,507,109 B2 | 12/2019 | Metchik et al. |
| 10,517,726 B2 | 12/2019 | Chau et al. |
| 10,524,792 B2 | 1/2020 | Hernandez et al. |
| 10,595,997 B2 | 3/2020 | Metchik et al. |
| 10,646,342 B1 | 5/2020 | Marr et al. |
| 10,779,837 B2 | 9/2020 | Lee et al. |
| D902,403 S | 11/2020 | Marsot et al. |
| 10,856,988 B2 | 12/2020 | McNiven et al. |
| 2002/0013571 A1 | 1/2002 | Goldfarb et al. |
| 2002/0183787 A1 | 12/2002 | Wahr et al. |
| 2003/0069593 A1 | 4/2003 | Tremulis et al. |
| 2003/0167071 A1 | 9/2003 | Martin et al. |
| 2004/0034365 A1 | 2/2004 | Lentz et al. |
| 2004/0044350 A1 | 3/2004 | Martin et al. |
| 2005/0267493 A1 | 12/2005 | Schreck et al. |
| 2007/0038293 A1 | 2/2007 | Goar St., et al. |

(56) References Cited

U.S. PATENT DOCUMENTS

| | | | |
|---|---|---|---|
| 2007/0197858 A1* | 8/2007 | Goldfarb | A61B 17/08 600/37 |
| 2010/0016958 A1* | 1/2010 | St. Goar | A61B 17/00234 623/2.36 |
| 2015/0182223 A1 | 7/2015 | Ketai et al. | |
| 2016/0067459 A1 | 3/2016 | Williams et al. | |
| 2016/0339204 A1 | 11/2016 | Williams et al. | |
| 2017/0042546 A1 | 2/2017 | Goldfarb et al. | |
| 2017/0049455 A1 | 2/2017 | Seguin | |
| 2017/0049571 A1* | 2/2017 | Gifford, III | A61F 2/2463 |
| 2017/0239048 A1 | 8/2017 | Goldfarb et al. | |
| 2017/0265994 A1 | 9/2017 | Krone | |
| 2018/0021133 A1 | 1/2018 | Barbarino | |
| 2018/0036119 A1 | 2/2018 | Wei et al. | |
| 2018/0092661 A1 | 4/2018 | Prabhu | |
| 2018/0146964 A1 | 5/2018 | Garcia et al. | |
| 2018/0235657 A1 | 8/2018 | Abunassar | |
| 2018/0242976 A1 | 8/2018 | Kizuka | |
| 2018/0243086 A1 | 8/2018 | Barbarino et al. | |
| 2018/0243087 A1* | 8/2018 | Kapadia | A61F 2/246 |
| 2018/0325671 A1 | 11/2018 | Abunassar et al. | |
| 2018/0344460 A1 | 12/2018 | Wei | |
| 2018/0353181 A1 | 12/2018 | Wei | |
| 2018/0360457 A1 | 12/2018 | Ellis et al. | |
| 2019/0053803 A1 | 2/2019 | Ketai et al. | |
| 2019/0125536 A1 | 5/2019 | Prabhu et al. | |
| 2019/0151041 A1 | 5/2019 | Ho et al. | |
| 2019/0151089 A1 | 5/2019 | Wei | |
| 2019/0159899 A1 | 5/2019 | Marsot et al. | |
| 2019/0167197 A1 | 6/2019 | Abunassar et al. | |
| 2019/0183571 A1 | 6/2019 | De Marchena | |
| 2019/0209293 A1 | 7/2019 | Metchik et al. | |
| 2019/0247187 A1 | 8/2019 | Kizuka | |
| 2019/0274831 A1 | 9/2019 | Prabhu | |
| 2019/0321597 A1 | 10/2019 | Van Hoven et al. | |
| 2019/0343630 A1 | 11/2019 | Kizuka | |
| 2019/0350702 A1 | 11/2019 | Hernandez | |
| 2019/0350710 A1 | 11/2019 | Ketai et al. | |
| 2019/0365536 A1 | 12/2019 | Prabhu | |
| 2020/0000473 A1 | 1/2020 | Dell et al. | |
| 2020/0060687 A1 | 2/2020 | Hernandez et al. | |
| 2020/0078173 A1 | 3/2020 | McNiven et al. | |
| 2020/0113678 A1 | 4/2020 | McCann et al. | |
| 2020/0121460 A1 | 4/2020 | Dale et al. | |
| 2020/0121894 A1 | 4/2020 | Prabhu et al. | |
| 2020/0187942 A1 | 6/2020 | Wei | |
| 2020/0205829 A1 | 7/2020 | Wei | |
| 2020/0245998 A1 | 8/2020 | Basude et al. | |
| 2020/0261107 A1 | 8/2020 | Cohen | |
| 2020/0281591 A1 | 9/2020 | Krone et al. | |
| 2020/0323528 A1 | 10/2020 | Khairkhahan | |
| 2020/0323549 A1 | 10/2020 | Goldfarb et al. | |
| 2020/0323634 A1 | 10/2020 | Von Oepen et al. | |
| 2020/0360018 A1 | 11/2020 | Dell et al. | |
| 2020/0367871 A1 | 11/2020 | Van Hoven et al. | |

FOREIGN PATENT DOCUMENTS

| | | |
|---|---|---|
| EP | 1 383 448 B1 | 6/2008 |
| FR | 2 768 324 A1 | 3/1999 |
| FR | 2 768 325 B1 | 11/1999 |
| WO | WO 91/01689 A1 | 2/1991 |
| WO | WO 92/12690 A1 | 8/1992 |
| WO | WO 94/018893 A1 | 9/1994 |
| WO | WO 96/32882 A1 | 10/1996 |
| WO | WO 97/27807 A1 | 8/1997 |
| WO | WO 98/07375 A1 | 2/1998 |
| WO | WO 99/07354 A2 | 2/1999 |
| WO | WO 99/13777 A1 | 3/1999 |
| WO | WO 99/15223 A1 | 4/1999 |
| WO | WO 00/03759 A2 | 1/2000 |
| WO | WO 00/60995 A2 | 10/2000 |
| WO | WO 01/28432 A1 | 4/2001 |
| WO | WO 03/020179 A1 | 3/2003 |
| WO | WO 03/049619 A2 | 6/2003 |
| WO | WO 2015/057289 A1 | 4/2015 |
| WO | WO 2016/178722 A1 | 11/2016 |
| WO | WO 2017/151566 A1 | 9/2017 |
| WO | WO 2018/093663 A1 | 5/2018 |
| WO | WO 2018/143560 A1 | 8/2018 |

OTHER PUBLICATIONS

U.S. Appl. No. 17/096,638, filed Nov. 12, 2020.
International Search Report and Written Opinion dated Feb. 25, 2021 in International Application No. PCT/US2020/060233.
Hahn et al., Accurate Measurement of Left Ventricular Outflow Tract Diameter: Comment on the Updated Recommendations for the Echocardiographic Assessment of Aortic Valve Stenosis, Journal of the American Society of Echocardiography 30(10):1038-1041 (2017).
U.S. Appl. 17/096,638, Jan. 18, 2023 Non-Final Office Action.

* cited by examiner

KIT WITH COAPTATION AID AND FIXATION SYSTEM AND METHODS FOR VALVE REPAIR

CROSS-REFERENCE TO RELATED APPLICATIONS

This application claims priority to U.S. Provisional Application No. 62/935,241, filed Nov. 14, 2019, the full disclosure of which is incorporated herein by reference in its entirety.

FIELD OF DISCLOSED SUBJECT MATTER

The disclosed subject matter is directed to medical devices and methods for the endovascular, percutaneous or minimally invasive surgical treatment of bodily tissues, such as tissue approximation or valve repair. More particularly, the present disclosure relates to repair of valves of the heart and venous valves.

Surgical repair of bodily tissues can involve tissue approximation and fastening of such tissues in the approximated arrangement. When repairing valves, tissue approximation includes coapting the leaflets of the valves in a therapeutic arrangement, which can then be maintained by fastening or fixing the leaflets. Such coaptation can be used to treat regurgitation, which commonly occurs in the mitral valve and in the tricuspid valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the mitral valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae, which connect the leaflets to the papillary muscles, the papillary muscles or the left ventricular wall can be damaged or otherwise dysfunctional. Commonly, the valve annulus can be damaged, dilated, or weakened, limiting the ability of the mitral valve to close adequately against the high pressures of the left ventricle. In some anatomies, the anterior mitral leaflet can be positioned at a significant distance away from the opposing posterior mitral leaflet or the anterior leaflet can dynamically move away from the region of coaptation with the posterior leaflet, and there is a need for repair assemblies enabling leaflet grasping in such or similar anatomies.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to a kit including a coaptation aid and a fixation system for repair of leaflets of a heart valve. The coaptation aid includes a coaptation catheter having an expandable member at a distal end thereof adapted to be introduced to a left ventricular outflow tract of a heart via a retrograde approach. The expandable member has a delivery configuration with a reduced cross-dimension and a deployed configuration with an expanded cross-dimension adapted to contact a ventricular side of a first leaflet of a heart valve and position the first leaflet generally proximate a coapting configuration with a second leaflet of the heart valve. The fixation system includes a delivery catheter having a distal end, and a fixation device removably coupled to the distal end of the delivery catheter and adapted to couple the first leaflet to the second leaflet of the heart valve.

The heart valve can be a mitral valve, the first leaflet can be an anterior leaflet and the second leaflet can be a posterior leaflet.

The coaptation catheter can further include a retractable sheath having an extended position and a retracted position. The expandable member can be an expandable scaffold. The retractable sheath can be adapted to retract from the extended position toward the retracted position to expose the expandable scaffold and allow the expandable member to transition from the delivery configuration toward the deployed configuration. The expandable scaffold can be a self-expanding scaffold. The self-expanding scaffold can include a tapered body having a distal portion with a larger cross dimension than a proximal portion. The self-expanding scaffold can have a proximal end portion and a distal end portion. The distal end portion can have at least one notch when in the deployed configuration to allow access of the fixation device to the first leaflet while positioned proximate the coapting configuration with the second leaflet. The self-expanding scaffold can have a marker proximate the at least one notch.

The expandable scaffold can be a balloon-expandable scaffold mounted on an expandable balloon of the coaptation catheter. The expandable scaffold can be adapted for release in the deployed configuration from the expandable balloon at the left ventricular outflow tract. The expandable scaffold can be made of a bioresorbable material. The expandable scaffold can further include one or more beneficial agents selected from the group consisting of an anti-inflammatory agent, an anti-coagulant agent, a thrombotic agent, an oxidative stress reducing agent, a growth factor, and a pro-healing agent.

The expandable member can be a balloon. The balloon can have a proximal end portion and a distal end portion. The distal end portion can have at least one recess formed therein when in the deployed configuration to allow access of the fixation device to the first leaflet while positioned proximate the coapting configuration with the second leaflet. The balloon can have a marker proximate the at least one recess. The coaptation catheter can include an inflation lumen in fluid communication with the balloon. The balloon can be an elongate balloon. The balloon can have a tapered body in the deployed configuration, which can have a distal portion with a larger cross dimension than a proximal portion.

The expandable member can further include a wireless sensor, which can provide one or more representative signals selected from the group consisting of left ventricular pressure signal, cardiac output measurement signal, vessel wall motion measurement signal, and ejection fraction measurement signal.

The coaptation catheter can be adapted for introduction via the retrograde approach through an access route selected from the group consisting of a femoral artery, a brachial artery, and a radial artery.

The expandable member can include a material selected from the group consisting of a metal, a super elastic material, a polymer, a bioresorable material and combinations thereof.

In accordance with the disclosed subject matter, a method for fixation of native leaflets of a heart valve using a coaptation aid includes introducing a coaptation aid with a coaptation catheter having an expandable member at a distal end thereof to a left ventricular outflow tract of a heart via a retrograde approach. The expandable member has a delivery configuration with a reduced cross-dimension and a deployed configuration with an expanded cross-dimension. The expandable member is in the delivery configuration while being introduced to the left ventricular outflow tract. The method also includes transitioning the expandable member from the delivery configuration toward the deployed configuration to contact a ventricular side of a first leaflet of a heart valve and position the first leaflet generally proximate a coapting configuration with a second leaflet of the heart valve. The method also includes delivering a fixation device to couple the first leaflet to the second leaflet of the heart valve.

The heart valve can be a mitral valve, the first leaflet can be an anterior leaflet and the second leaflet can be a posterior leaflet.

The method can further include, after delivering the fixation device, transitioning the expandable member toward the delivery configuration and withdrawing the coaptation aid from the left ventricular outflow tract of the heart.

The method for fixation of native leaflets of a heart valve using a coaptation aid can include any of the features described above for the kit. For example, the expandable member can be an expandable scaffold. The method can further include releasing the expandable scaffold from the coaptation catheter in the deployed configuration at the left ventricular outflow tract. The expandable scaffold can be made of a bioresorable material. The coaptation catheter can further include a retractable sheath. The method, prior to transitioning the expandable member, can further include aligning a distal tip of the retractable sheath with a hinge point of the first leaflet, and retracting the retractable sheath to expose the expandable member. Introducing the coaptation aid can include using an access route from the group consisting of a femoral artery, a brachial artery, and a radial artery.

DETAILED DESCRIPTION

Reference will now be made in detail to various exemplary embodiments of the disclosed subject matter, which are illustrated in the accompanying drawings. A technique for mitral valve repair, which relies on suturing adjacent segments of the opposed valve leaflets together is referred to as the "bow-tie" or "edge-to-edge" technique. The kit, devices and methods of the disclosed subject matter provide for repair of leaflets of a heart valve, such as edge-to-edge valve repair for patients having various conditions, such as a regurgitant mitral valve. Such kits, devices and systems likewise can be useful for repair of tissues in the body other than heart valves. The kits, devices and systems disclosed herein do not require open chest access and are capable of being performed endovascularly, i.e., using devices, such as a catheter, which are advanced to the heart from a point in the patient's vasculature remote from the heart.

Figure 1A:
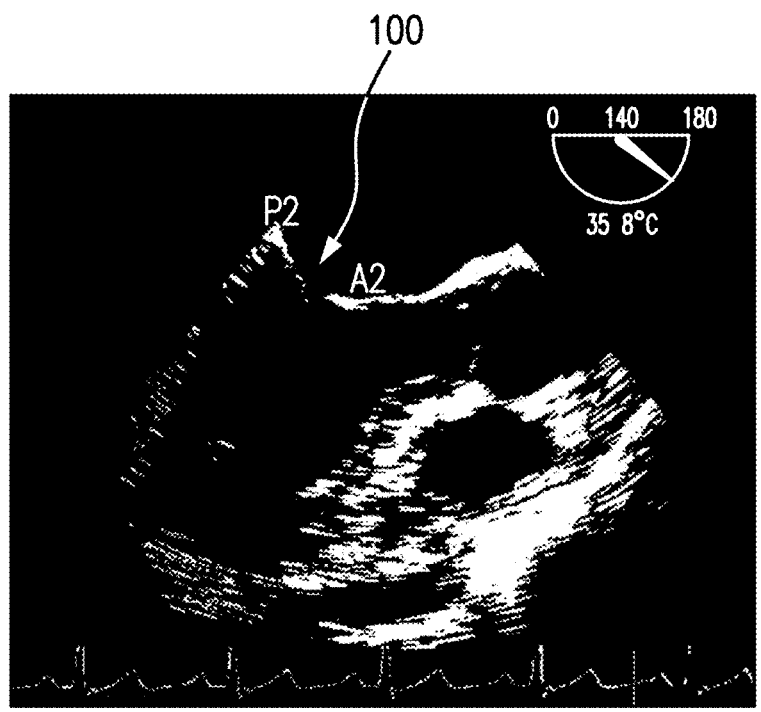
FIG. 1A is a trans-esophageal echocardiography image of a mitral valve.

For the purpose of illustration and not limitation, FIG. 1A is trans-esophageal echocardiography image of a heart valve 100, specifically a left ventricular outflow tract view of a mitral valve. Such a trans-esophageal echocardiography can be used for visualization during an edge-to-edge mitral valve repair procedure.

Figure 1B:
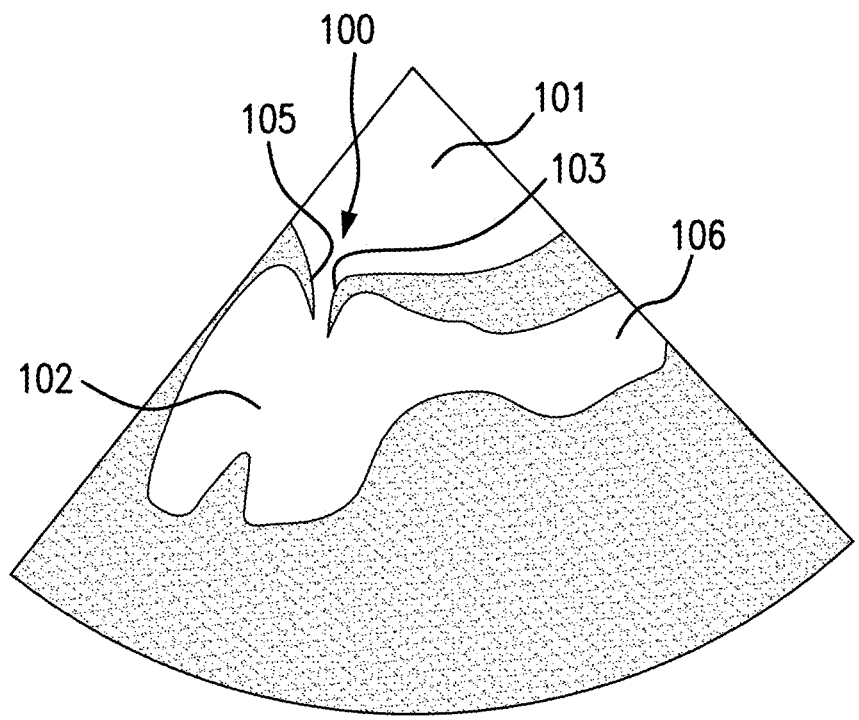
FIG. 1B is a schematic illustration of the mitral valve anatomy of FIG. 1A.

FIG. 1B is a schematic illustration of the mitral valve 100 of FIG. 1A and depicts the mitral anatomy including an anterior mitral leaflet 103 and a posterior mitral leaflet 105 that open and close to control blood flow from the left atrium 101 to the left ventricle 102 and further through the left ventricular outflow tract 106. FIG. 1B (and the trans-esophageal echocardiography of FIG. 1A) shows a mild regurgitation disease state, where the mid-sections of the anterior mitral leaflet 103 (A2 in FIG. 1A) and posterior mitral leaflet 105 (P2 in FIG. 1A) are shown to be non-coapting, but to be reasonably close to each other during cardiac systole. Edge-to-edge valve repair can be performed using a leaflet fixation device by targeting each leaflet to improve coaptation of the anterior and posterior mitral leaflets and reduce regurgitation.

Figure 1C:
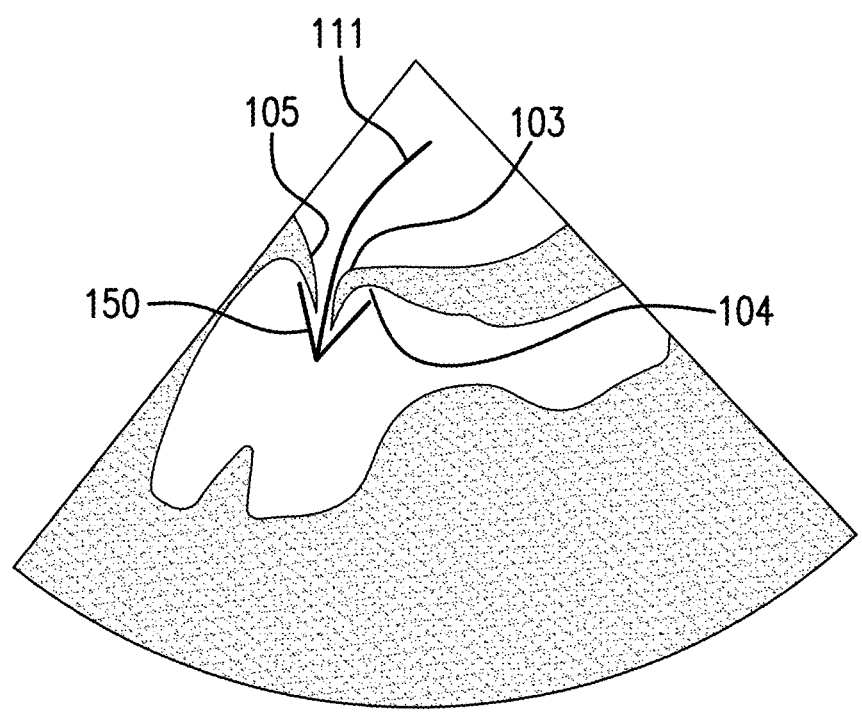
FIG. 1C is a schematic illustration of the mitral valve anatomy of FIG. 1A having a leaflet fixation device for edge-to-edge repair positioned to reach both leaflets of the mitral valve.

As illustrated in FIG. 1C, when performing transcatheter edge-to-edge repair, a leaflet fixation device 150, is delivered on the distal end of a catheter shaft 111 such that the opposing leaflets 103, 105 are inserted within a leaflet fixation device 150 and brought together into coaptation. These fixation devices can use arms to contact the distal side 104 of leaflets. Once the arms are positioned to stabilize the leaflets in a beating heart, gripping elements or the like contact the atrial side of the leaflets to capture the leaflets. Once both opposing leaflets are captured, the fixation device 150 can be closed such that the leaflets are pulled and brought into coaptation, which results in a reduction in valvular regurgitation during ventricular systole.

Figure 2A:
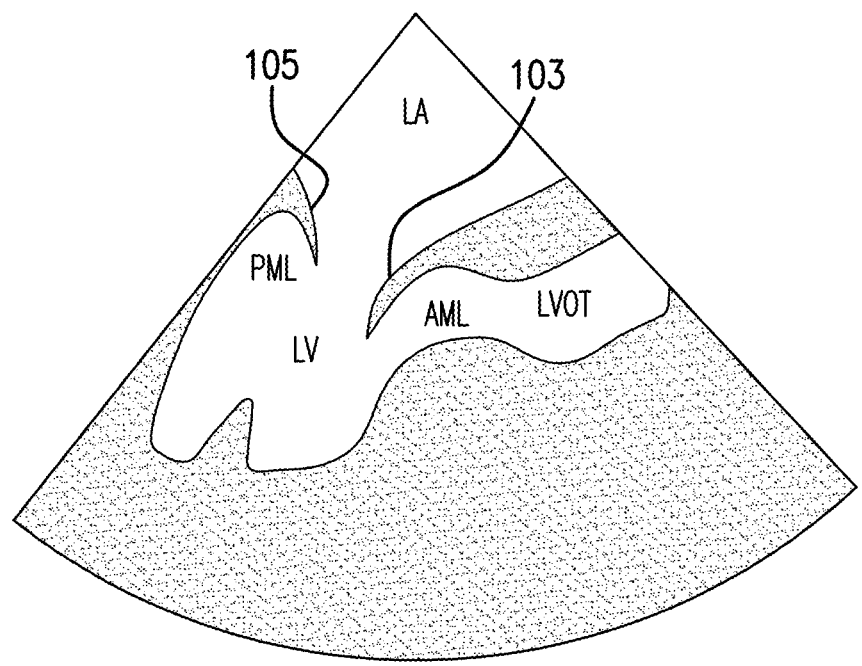
FIG. 2A is a schematic illustration of mitral valve anatomy having a depressed anterior mitral leaflet.
Figure 2B:
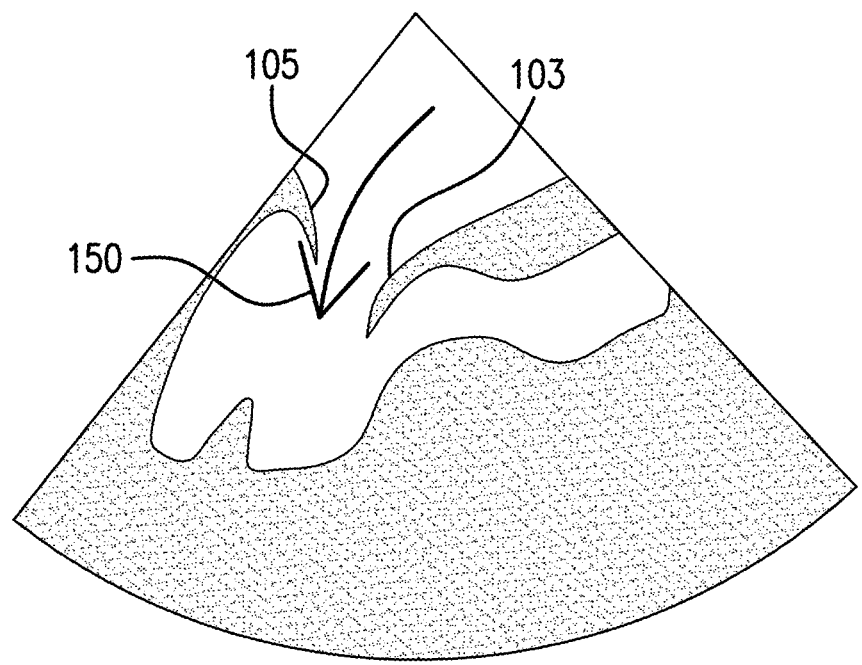
FIG. 2B is a schematic illustration of the mitral valve anatomy of FIG. 2A having a leaflet fixation device for edge-to-edge repair positioned proximate the posterior leaflet and not capable of reaching the anterior mitral leaflet.

However, leaflet locations can vary from patient to patient, and in certain patients it can be difficult to reach and capture both leaflets using fixation devices alone. For example, FIG. 2A depicts a mitral valve anatomy demonstrating a large coaptation gap, with the anterior mitral leaflet 103 depressed or spaced at a distance from the posterior mitral leaflet 105. As illustrated in FIG. 2B, because the anterior mitral leaflet 103 is significantly spaced from the posterior mitral leaflet 105, the leaflet fixation device 150 may not be able to reach the anterior mitral leaflet 103, and successful edge-to-edge repair may be difficult, requiring a great deal of procedural skill and time. The leaflet grasping procedure can be further complicated by erratic leaflet motion, such as systolic anterior motion of the anterior mitral valve leaflet. Further, if only a minimal amount of leaflet can be inserted within the arms and gripping elements during the procedure based upon the large gap, mitral regurgitation may not be significantly improved by a single implantation and additional devices or further intervention may be needed to reduce the mitral regurgitation.

To address these problems, generally, and as set forth in greater detail below, the disclosed subject matter includes a kit with a coaptation aid and a fixation system for repair of leaflets of a heart valve. The coaptation aid includes a coaptation catheter having an expandable member at a distal end thereof adapted to be introduced to a left ventricular outflow tract of a heart via a retrograde approach. The expandable member has a delivery configuration with a reduced cross-dimension and a deployed configuration with an expanded cross-dimension adapted to contact a ventricular side of an anterior leaflet of a mitral valve and position the anterior leaflet generally proximate a coapting configuration with a posterior leaflet of the mitral valve. The fixation system includes a delivery catheter having a distal end, and a fixation device removably coupled to the distal end of the delivery catheter and adapted to couple the anterior leaflet to the posterior leaflet of the mitral valve Likewise, as further described in conjunction with the kit of the disclosed subject matter, a method for fixation of native leaflets of a mitral valve using a coaptation aid is provided. The method includes introducing a coaptation aid with a coaptation catheter having an expandable member at a distal end thereof to a left ventricular outflow tract of a heart via a retrograde approach. The expandable member has a delivery configuration with a reduced cross-dimension and a deployed configuration with an expanded cross-dimension. The expandable member is in the delivery configuration while being introduced to the left ventricular outflow tract. The method also includes transitioning the expandable member from the delivery configuration toward the deployed configuration to contact a ventricular side of an anterior leaflet of a mitral valve and position the anterior leaflet generally proximate a coapting configuration with a posterior leaflet of the mitral valve. The method also includes delivering a fixation device to couple the anterior leaflet to the posterior leaflet of the mitral valve.

The coaptation aid thus can improve the ease of leaflet grasping and capture by providing a mechanism to temporarily facilitate positioning and stabilization of a leaflet, such as the anterior mitral leaflet, during an edge-to-edge repair procedure.

Figure 3A:
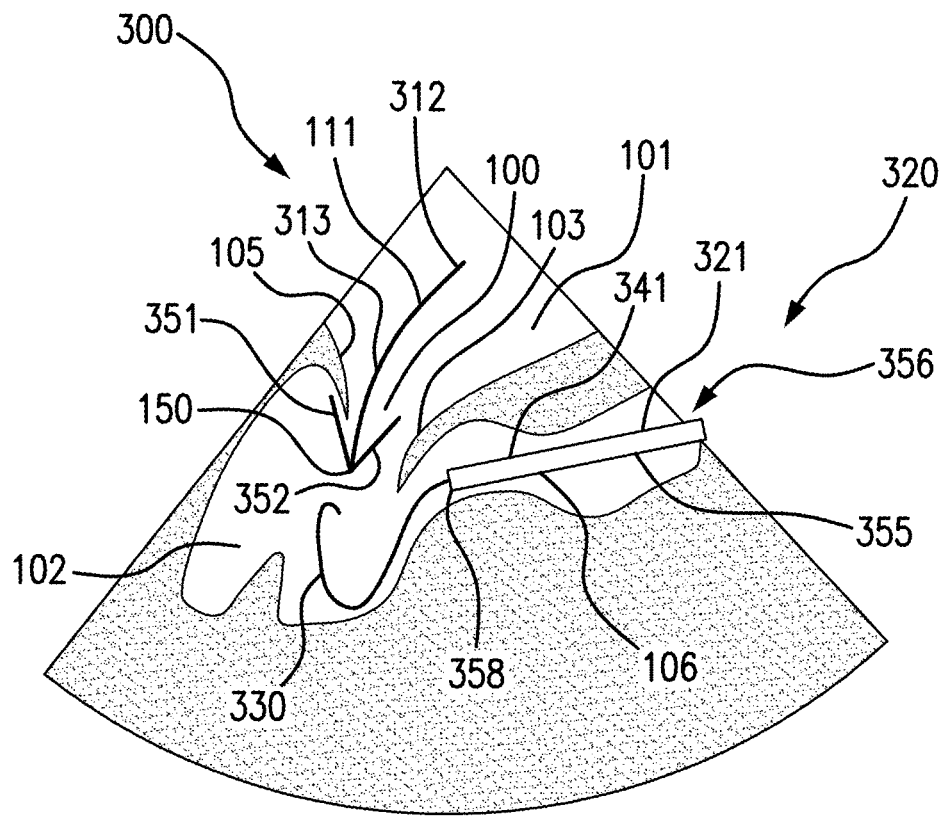
FIGS. 3A, 3B, and 3C are sequential schematic illustrations of a method for fixation of native leaflets of a mitral valve using a kit including a coaptation aid and a fixation system in accordance with the disclosed subject matter.
Figure 3B:
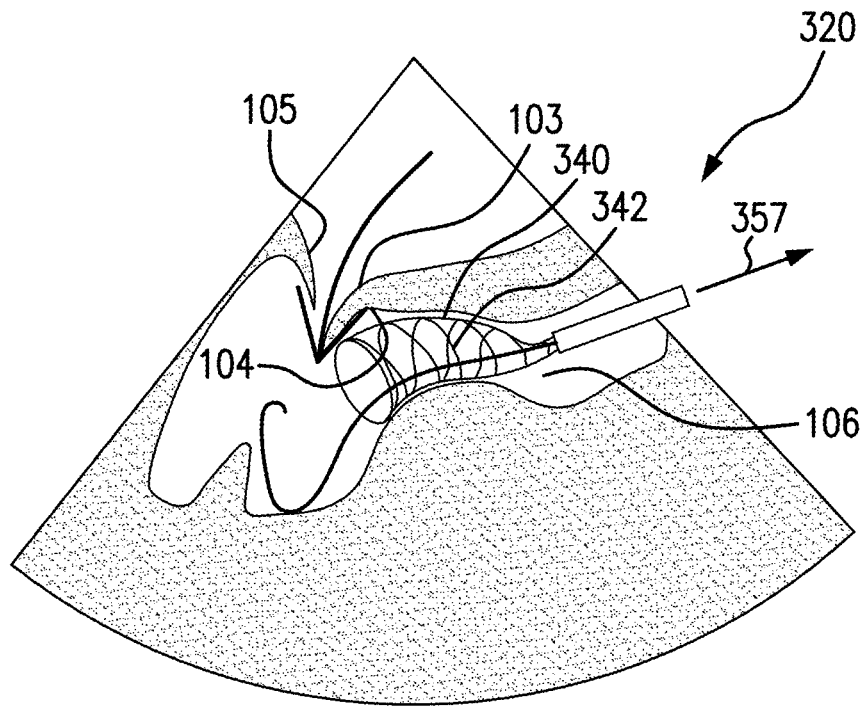

Referring to FIGS. 3A and 3B, for purpose of illustration and not limitation, an exemplary kit includes coaptation aid 320 with a coaptation catheter 321 for delivering an expandable member 340 to a left ventricular outflow tract 106 of a heart. The expandable member 340 has a delivery configuration 341 with a reduced cross-dimension (in FIG. 3A expandable member is within coaptation catheter 321) and a deployed configuration 342 as shown in FIG. 3B with an expanded cross-dimension adapted to contact a ventricular side 104 of an anterior leaflet 103 of a mitral valve and position the anterior leaflet generally proximate a coapting configuration with a posterior leaflet 105 of the mitral valve. The kit also includes a fixation system including a delivery catheter 300 having a distal end 313, and a fixation device 150 removably coupled to the distal end of the delivery catheter and adapted to couple the anterior leaflet 103 to the posterior leaflet 105 of the mitral valve.

With continued reference to FIG. 3A, the leaflet fixation device 150, e.g., a clip, can be delivered via a separate delivery catheter 300 including an elongate catheter shaft 111 having a proximal portion 312 and a distal end 313. The leaflet fixation device 150 is releasably coupled to the distal end 313 of the catheter shaft and is configured to grasp and couple two (or more) leaflets together. Although a number of edge-to-edge leaflet repair devices are known, for purpose of understanding and not limitation, reference will be made herein to a fixation device having a first gripper assembly 351 and a second gripper assembly 352 to capture the native leaflets, wherein each gripper assembly includes a movable arm and gripper element to capture a leaflet therebetween. Additional features and alternative embodiments of suitable catheters for delivering the leaflet fixation device and the expandable member (including details of the proximal portions) are set forth, for example, in U.S. Pat. No. 7,226,467 to Lucatero et al., U.S. Pat. No. 7,563,267 to Goldfarb et al., U.S. Pat. No. 7,655,015 to Goldfarb et al., U.S. Pat. No. 7,736,388 to Goldfarb et al., U.S. Pat. No. 7,811,296 to Goldfarb et al., U.S. Pat. No. 8,057,493 to Goldfarb et al., U.S. Pat. No. 8,303,608 to Goldfarb et al., U.S. Pat. No. 8,500,761 to Goldfarb et al., U.S. Pat. No. 8,734,505 to Goldfarb et al., U.S. Pat. No. 8,740,920 to Goldfarb et al., U.S. Pat. No. 9,510,829 to Goldfarb et al., U.S. Pat. No. 7,635,329 to Goldfarb et al., U.S. Patent Application Publication No. 2017/0042546 to Goldfarb et al., U.S. Patent Application Publication No. 2017/0239048 to Goldfarb et al., U.S. Patent Application Publication No. 2018/0325671 to Abunassar et al., the contents of each of which is incorporated by reference in its entirety herein (collectively "the Representative Patent Publications").

In use, the delivery catheter 300 is introduced proximate the native leaflets of a heart valve 100. For illustration and not limitation and as embodied herein, the delivery catheter 300 can be delivered via an antegrade approach from a patient's left atrium 101 to the left ventricle 102. For example, in a transcatheter approach, the delivery catheter 300 can be introduced in a femoral vein and advanced through the inferior vena cava into the heart, across a penetration in the interatrial septum (i.e., a transseptal approach), and to the mitral valve from the atrium toward the ventricle. Details of various suitable approaches for leaflet repair are described in, for example, the Representative Patent Publications.

Once located proximate native leaflets of a heart valve 100, the first gripper assembly 351 of the leaflet fixation device 150 is deployed to capture a first native leaflet, such as the posterior mitral leaflet 105, as depicted in FIG. 3A. For example, arms of the fixation device 150 can be aligned generally perpendicular to a line of coaptation of the mitral valve, with the device positioned so that a first arm contacts the ventricular surface of the posterior mitral leaflet 105. A corresponding gripping element can remain on the atrial side of the valve leaflet so that the leaflet lies between the gripping element and the arm. As embodied herein, the first gripping element can be lowered toward the arm so that the leaflet is captured and held therebetween. Alternatively, the leaflet can be held with the arm underneath without lowering the gripping element until later in the procedure. Additional features and alternative embodiments of leaflet fixation devices and the grasping and capture process are described in, for example, the Representative Patent Publications.

In certain anatomies where the anterior mitral leaflet is significantly spaced from the posterior mitral leaflet or has dynamically moved away from the region of coaptation where edge-to-edge repair using the leaflet fixation device would not be possible as shown in FIG. 3A, the coaptation aid of the disclosed subject matter can be used to position the anterior mitral leaflet close to the posterior mitral leaflet to allow for edge-to-edge repair.

As shown in FIG. 3A, to introduce the coaptation aid of the disclosed subject matter, a guide wire 330 can be introduced to the left ventricular outflow tract 106 via retrograde approach, which can include an access route selected from the group consisting of a femoral artery, a brachial artery, and a radial artery. Any suitable guidewire known in the art can be used for such delivery. The coaptation catheter 321 can be delivered to the left ventricular outflow tract over guide wire 330. During introduction to the left ventricular outflow tract, the expandable member 340 is in the delivery configuration 341, for example located within the coaptation catheter 321. Once positioned in the left ventricular outflow tract proximate the anterior mitral leaflet 103, the expandable member 340 is allowed to transition from the delivery configuration 341 (FIG. 3A) toward the deployed configuration 342 (FIG. 3B) to contact a ventricular side 104 of an anterior leaflet 103 of a mitral valve and position the anterior leaflet generally proximate a coapting configuration with a posterior leaflet 105 of the mitral valve as shown in FIG. 3B.

Figure 3C:
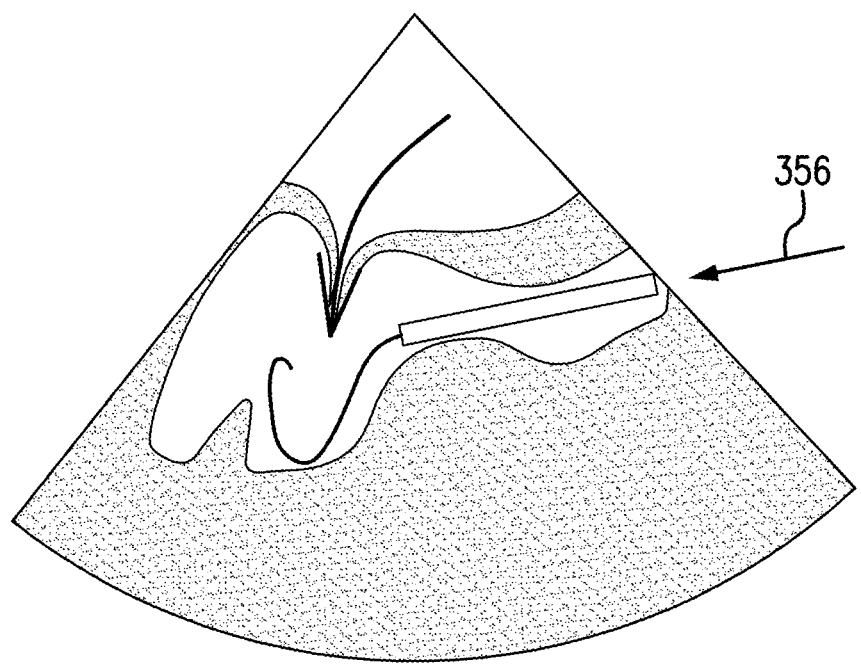

For example, and as depicted schematically in FIGS. 3A, 3B, and 3C, the coaptation catheter can include a retractable sheath 355 having an extended position 356 and a retracted position 357. The retractable sheath can be adapted to retract from the extended position 356 shown in FIG. 3A toward the retracted position 357 shown in FIG. 3B to expose the expandable member 340 and allow the expandable member to transition from the delivery configuration 341 toward the deployed configuration 342. The method, prior to transitioning the expandable member, can further include aligning a distal tip 358 of the retractable sheath with a hinge point of the anterior leaflet 103. Once located in the desired position, the sheath 355 can be partially retracted as shown in FIG. 3B to expose the expandable member 340. Once expanded, expandable member 340 contacts the underside or distal side 104 of the anterior leaflet 103 to position, e.g., prop, the leaflet into a favorable location for deployment of the leaflet fixation device 150, described below.

Depending upon the desired construction as disclosed herein, the expandable member 340 can include a material selected from the group consisting of a metal, a super elastic material, a polymer, a bioresorable material and combinations thereof. For example, the expandable member can be a self-expanding scaffold, such as a scaffold contained within a sheath, or a balloon expandable scaffold mounted on a balloon of the coaptation catheter. Alternatively, and as contemplated by the disclosed subject matter, and as described further below, the expandable member can be a balloon.

Figure 4:
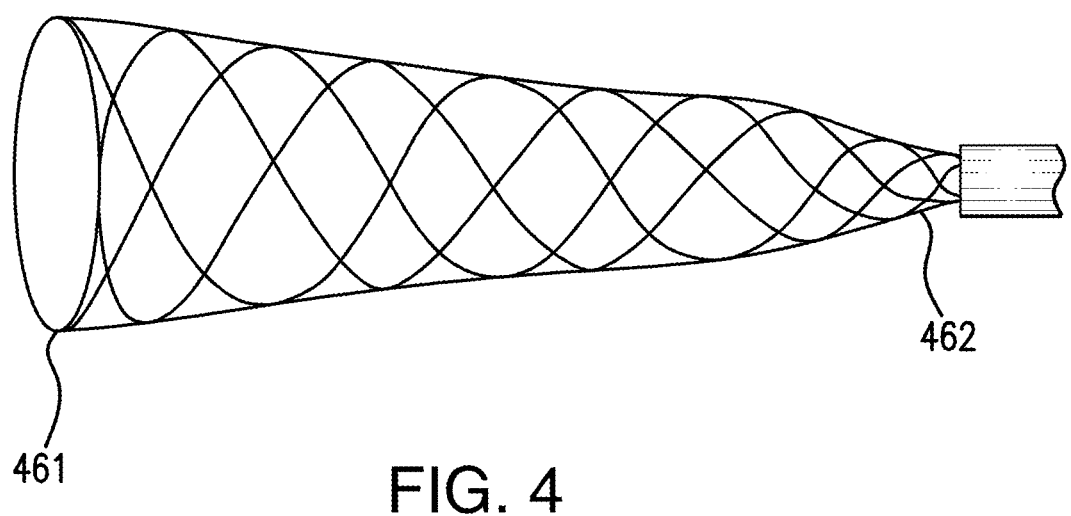
FIG. 4 is a front view of an exemplary embodiment of a coaptation aid for fixation of leaflets of a heart valve in accordance with the disclosed subject matter.

For example and in accordance with the disclosed subject matter, the expandable member can be an expandable scaffold as depicted schematically for purpose of illustration and not limitation in FIG. 4. The expandable scaffold can have a variety of suitable shapes, such as an elongate cylinder or a tapered cylinder as shown, as long as it includes a sufficient diameter to engage with the underside of the anterior mitral leaflet. For example, the scaffold can be formed with a larger cross dimension at a distal portion 461 and taper continuously to a smaller cross dimension at a proximal portion 462. The tapered configuration can increase the chance of achieving favorable contact with the anterior mitral leaflet 103 at a point of the leaflet hinge point, or even farther out toward the leaflet tip near the region of coaptation.

The expandable scaffold can be self-expanding and can be formed from a shape memory material, such as nitinol, which is well known in the field of stents and frames for heart valve replacement devices. The scaffold can be formed by laser cutting from a tube or can be shaped of nitinol wire on a mandrel as known in the art. The scaffold could also be made other materials, such as polymers. The scaffold can include any structure known in the art, including ring and connector, spiral, open or closed basket or cell pattern, or the like. The scaffold can have a sparse construction to reduce interaction with chordae tendineae below the native valve.

Figure 5:
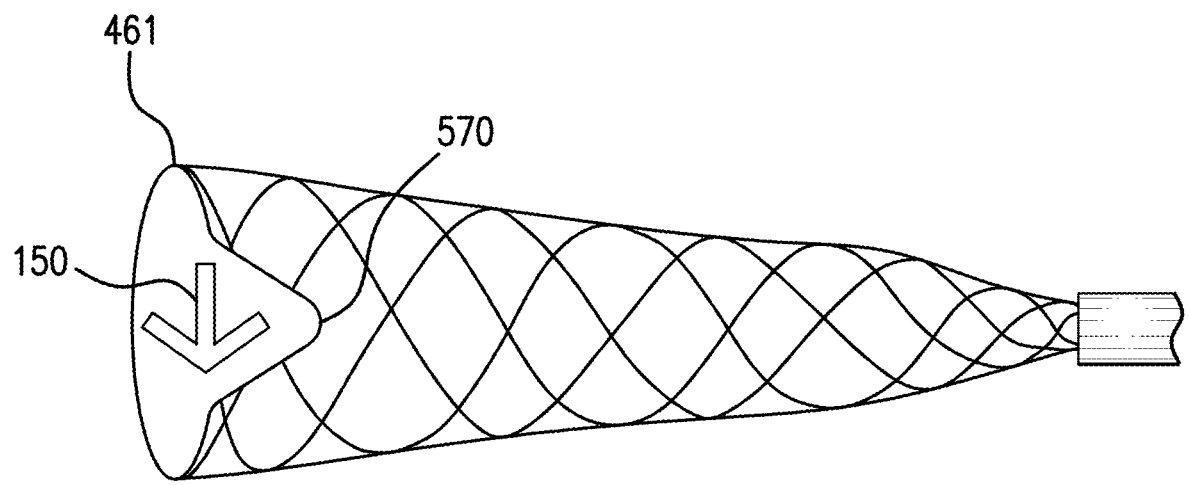
FIG. 5 is a front view of an alternative exemplary embodiment of a coaptation aid for fixation of leaflets of a heart valve in accordance with the disclosed subject matter.

In accordance with another aspect of the disclosed subject matter, and with reference to FIG. 5 for illustration and not limitation, the distal portion 461 of the scaffold can be provided with at least one recess or notch 570 at its distal end. The notch, when in the deployed configuration, can allow the fixation device 150 to access the anterior leaflet while positioned proximate the coapting configuration with the posterior leaflet. As embodied herein, the notch is placed over the middle of the anterior leaflet 103 such that the scaffold remains clear of the arm of the fixation device 150 being positioned and closed at the leaflet. Additional notches could be positioned at many locations along the scaffold to avoid undesirable interactions with the papillary muscles or chordae tendineae.

Figure 6:
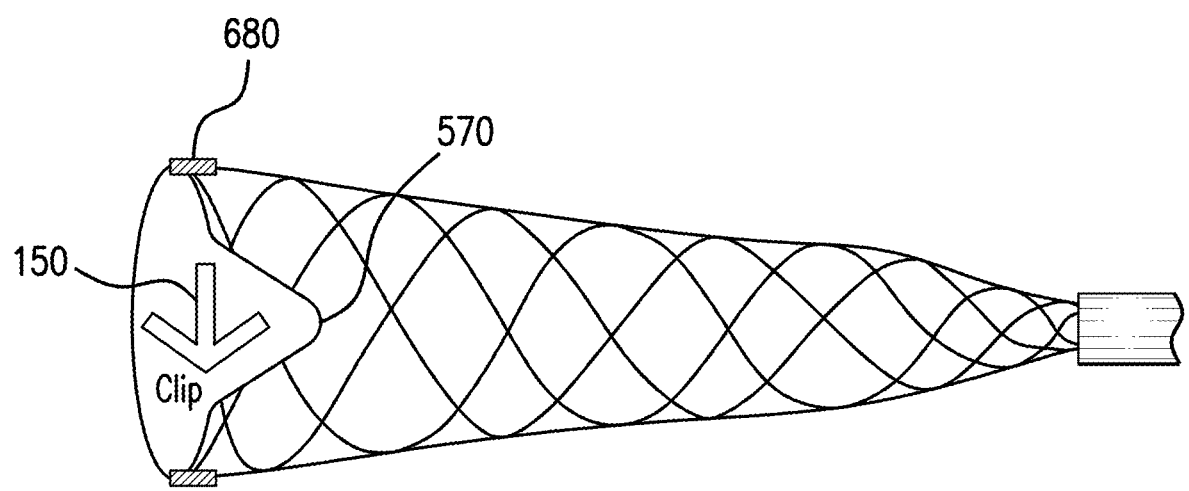
FIG. 6 is a front view of the exemplary embodiment of a coaptation aid with a fixation device for fixation of leaflets of a heart valve as shown in FIG. 5 and further having a sensor in accordance with the disclosed subject matter.

In accordance with another aspect of the disclosed subject matter, and with reference to FIG. 6 for illustration and not limitation, the expandable scaffold can include a marker 680 proximate the at least one notch 570. For example, a single marker, pairs of markers, or an array of markers proximate the notch at the distal end of the scaffold can be aligned with the target region of the leaflet for leaflet fixation such as the middle of the anterior leaflet. The markers can be radiopaque or echogenic and can be used to improve the position of the notch during a procedure, e.g., by locating the notch at the twelve o'clock position as the catheter is torqued.

Figure 7:
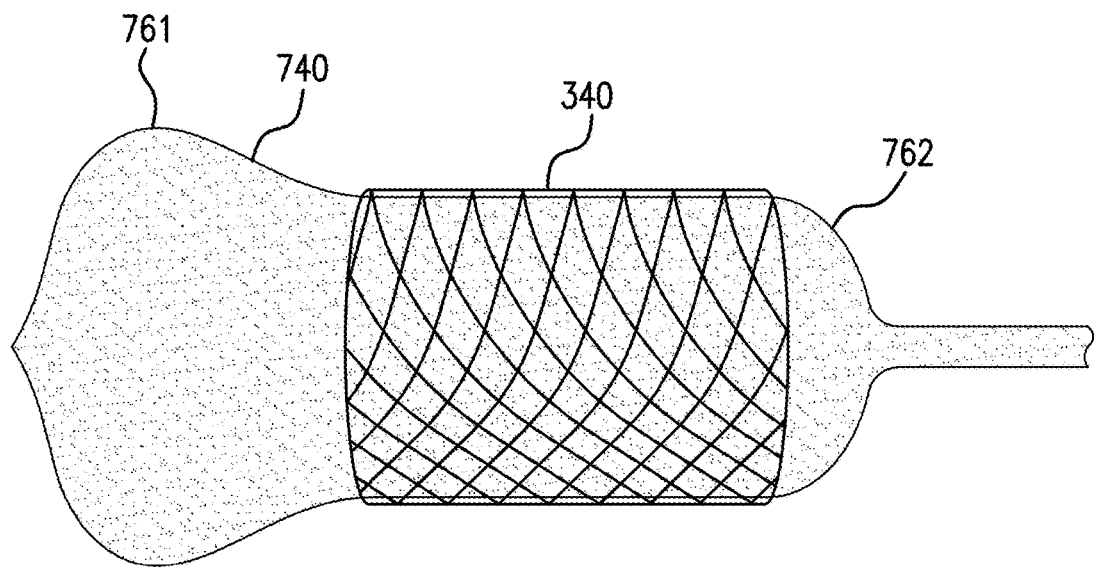
FIG. 7 is a front view of an alternative exemplary embodiment of a coaptation aid for fixation of leaflets of a heart valve in accordance with the disclosed subject matter.

In accordance with another aspect of the disclosed subject matter, and with reference to FIG. 7 for illustration and not limitation, the expandable scaffold 340 can adapted for release from the coaptation catheter 321 in the deployed configuration at the left ventricular outflow tract 106. For example, the expandable scaffold can be mounted on a balloon 740 of the coaptation catheter 321. The balloon can have any suitable shape for delivering the expandable scaffold such as a cylinder. Alternatively, the balloon can include a tapered cylinder in the deployed configuration with a distal portion 761 with a larger cross dimension than a proximal portion 762. In such embodiments, the scaffold can be positioned on a proximal portion of the balloon so that it is delivered within the left ventricular outflow tract yet does not interfere with the function of the mitral valve after implant. The tapered balloon distal portion extending beyond the scaffold can be used to position the anterior leaflet proximate the coapting configuration with the posterior leaflet prior to deploying the fixation device. Furthermore, the scaffold can be short enough to avoid blocking the aortic valve and can be used to prevent left ventricular outflow obstruction (LVOT) after deployment.

For example, the scaffold can have a length of at least 2 to 3 centimeters in length and preferably 4 to 6 centimeters in length in order to encompass and support a full length of an anterior mitral valve leaflet with a significant margin included. Further, the scaffold can preferably have a diameter that approximately corresponds to the left ventricular outflow tract (LVOT) diameter for a given patient, which is estimated in millimeters in the literature to be 5.7×body surface area+12.1. (Hahn et al., Accurate Measurement of Left Ventricular Outflow Tract Diameter: Comment on the Updated Recommendations for the Echocardiographic Assessment of Aortic Valve Stenosis, Journal of the American Society of Echocardiography Volume 30 Number 10). The scaffold can have an open cell pattern (for more conformability) or a closed cell pattern (for more radial support) with any combination and pattern transitions throughout its length. The scaffold can be made radially stiff in sections that secure the scaffold in the LVOT, while the leading edge that contacts leaflets can be made with narrower or thinner struts to reduce the potential for damaging leaflets or subvalvular anatomic structures.

In accordance with the disclosed subject matter, the expandable scaffold adapted for release can be made of a bioresorbable material and intended to remain in the body for a period of time (e.g., days, weeks, months, or years) after implant. For example, the scaffold can be made of biodegradable polymers like poly-L-lactide.

Thus, in addition to providing the positioning benefits of the coaptation aid embodiments described herein, the release of the scaffold can also be used to provide additional benefits. For example, the expandable scaffold can further include and elute one or more beneficial agent, such as an anti-inflammatory agent, an anti-coagulant agent, a thrombotic agent, an oxidative stress reducing agent, a growth factor, a pro-healing agent, or the like. The presence of the scaffold can also aid in the prevention of left ventricular outflow tract obstruction if a used in combination with a replacement mitral valve of a size that could otherwise compromise the left ventricular outflow tract.

Figure 8:
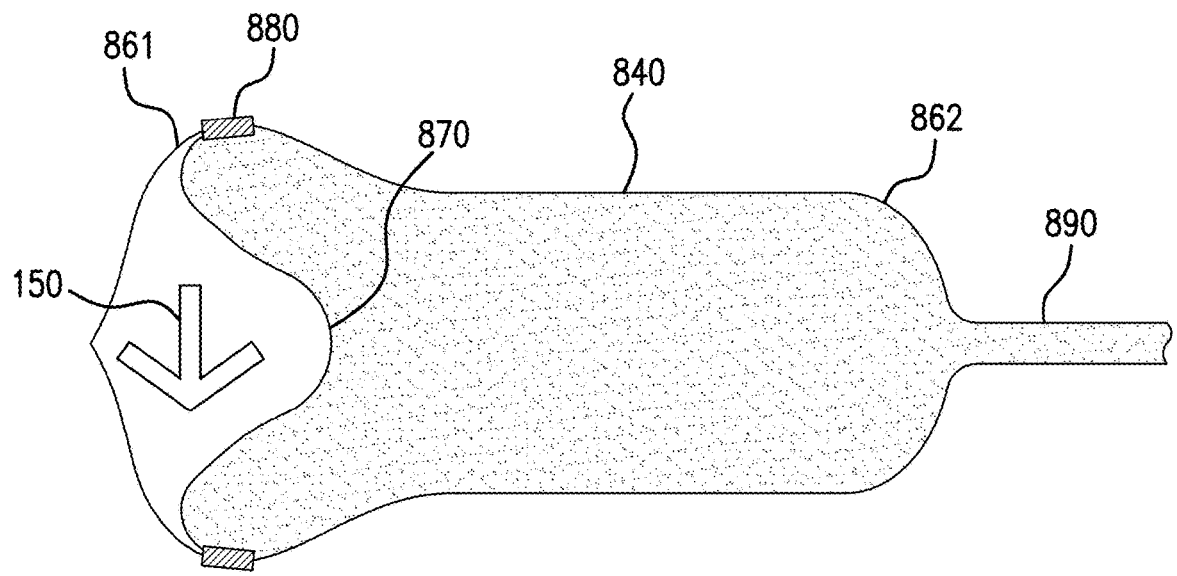
FIG. 8 is a front view of another exemplary embodiment of a coaptation aid for fixation of leaflets of a heart valve in accordance with the disclosed subject matter.

In accordance with another aspect of the disclosed subject matter, and as shown in FIG. 8 for the purpose of illustration and not limitation, the expandable member 340 can be a balloon 840, such as an elongate balloon. The balloon can be cylindrical or can have a tapered body in the deployed configuration with a distal portion 861 with a larger cross dimension than a proximal portion 862.

Furthermore, the distal end portion 861 of balloon 840 can have at least one recess 870 formed therein. Like the notch 570 described above, in the deployed configuration, the recess 870 in the balloon allows access of the fixation device 150 to the anterior leaflet while positioned proximate the coapting configuration with the posterior leaflet. In addition, the balloon 840 can have a marker 880 proximate the at least one recess 870. Additionally or alternatively, the balloon 840 can be filled with contrast media to aid in visualization and positioning of the balloon.

The coaptation catheter 321 can include an inflation lumen 890 in fluid communication with the balloon 840. Thus the interior of the balloon is in a fluid flow relation with an inflation lumen extending along a length of the coaptation catheter, and fluid under pressure can thereby be supplied to the interior of the balloon through the inflation lumen to expand the balloon. The balloon can include marker bands (e.g., made of platinum/iridium), for example positioned on the proximal and distal sections of the balloon or catheter.

In accordance with the disclosed subject matter, the balloon 840 can be composed of a wide variety of suitable materials, for example, nylons, co-polyamides such as PEBAX®, polyester, co-polyester, polyurethane, polyethylene, or the like. The balloon 840 can comprise a single layer or multiple layers of polymer material. Details of suitable multilayer balloons are described in U.S. Pat. Nos. 7,828,766, 8,394,055, and 9,132,259, the contents of each of which are herein incorporated by reference in their entirety. The balloon can have wings and be folded as known in the art.

As embodied herein, the balloon 840 can be a relatively high rupture pressure, non-compliant balloon, which can have a rupture pressure of at least about 20-30 atm. Alternatively, the balloon can be made to function in a more conforming manner and can be made with a thin wall in order to provide a more compliant and atraumatic impingement on the chordae and leaflet structures. The balloon can be made porous to permit blood flow to pass through the coaptation aid during a procedure. Additionally or alternatively, the balloon can be fashioned with a toroidal geometry such that blood flow can pass through its center. Since the left ventricular outflow tract is generally elliptical in shape, an aligning elliptical balloon geometry can also be used. Further, the balloon can be tapered, can have a curved profile geometry, or can be manufactured with intentional kinks in order to conform to the apex of the heart and turn upward toward the anterior mitral valve leaflet. Any combination of the above-mentioned features is contemplated in this application.

The balloon can additionally include any of any of the features described above for the expandable scaffold. Additional suitable materials, configurations, and methods of manufacture of the balloon 140 and related disclosure are provided in U.S. Pat. Nos. 7,074,206, 8,052,638, 10,086,175, U.S. Patent Publication No. 2016/0339204 and U.S. Patent Publication No. 2016/0067459, the contents of each of which is hereby incorporated by reference in its entirety.

Further in accordance with the disclosed subject matter, the expandable member can further include a wireless sensor, which can provide one or more representative signals, such as left ventricular pressure signal, cardiac output measurement signal, vessel wall motion measurement signal, ejection fraction measurement signal, or the like. For example, cardiac output can be estimated intraprocedurally to determine the impact of intra-procedural blood flow obstruction occurring during leaflet stabilization and for evaluation of the degree of therapeutic improvement achieved during a valve repair procedure. This cardiac output (flow rate) feedback, along with pressure gradient measurements can aid a physician in balancing the effectiveness and safety risks of performing a coaptation aided mitral valve repair.

The expandable member (scaffold or balloon) can have any suitable dimensions, for example including a cross sectional area and length of 4-6 $cm^2$ and 4-6 cm, respectively. The expanding member can be tapered in profile, curved to conform around the apex of the heart, or kinked to easily turn upward into contact with an anterior mitral valve leaflet to provide support during mitral valve repair procedures.

Returning now to the method of leaflet repair, in the deployed configuration 342 of FIG. 3B, with the coaptation aid 320 including expandable member 340 (scaffold or balloon 840) acting as a stabilizing support for the anterior mitral leaflet 103, the fixation device 150 can be more easily used to simultaneously grasp both leaflets. The arm of the second gripper assembly 352 of the leaflet fixation device 150 is deployed to contact the ventricular surface 104 of and grasp the anterior mitral leaflet 103. The corresponding gripping element can remain on the atrial side of the leaflet so that the leaflet lies between the gripping element and the arm.

If needed, the fixation device 150 can be repeatedly manipulated to reposition the device so that the leaflets are properly grasped at a desired location. Repositioning can be achieved with the fixation device 150 in an open position. For example, the coaptation aid 320 can be manipulated to reposition the leaflets, such as by further expanding or retracting the expandable member 340 to better position the anterior mitral leaflet 103. As embodied herein, the delivery catheter 300 can be longitudinally rotated to apply different tension on the leaflet via the expandable member 340 to better position the leaflet for capture. Regurgitation of the valve can also be checked while the fixation device 150 is in the open position. If regurgitation is not satisfactorily reduced, the fixation device 150 can be repositioned, and regurgitation checked again until desired results are achieved.

Once the fixation device 150 has been positioned in a desired location relative to the valve leaflets, the leaflets can then be captured between the gripping elements and the arms. As noted above, the first gripping element may already have been lowered to capture the posterior leaflet. If so, the second gripping element is lowered to capture the anterior leaflet. Alternatively, if the posterior leaflet has not yet been captured, both gripping elements can be lowered toward the arms so that the leaflets are held and captured therebetween, either simultaneously or sequentially. Once both leaflets are captured, the arms can be closed to a tight arm angle to bring each leaflet into central coaptation to reduce regurgitation. The arms can further be locked to the prevent the device from moving toward an open position.

Once completed, the coaptation aid 320 can be removed by transitioning the expandable member 340 (scaffold or balloon) toward the delivery configuration 241. For example, the balloon can be deflated or the scaffold resheathed within the retractable sheath as shown in FIG. 3, to return the delivery system to a low-profile configuration. With the coaptation aid removed, the repair of the leaflets or tissue can be observed by non-invasive visualization techniques, such as echocardiography, to ensure the desired outcome. If the repair is not desired, the fixation device 150 can be repositioned or retrieved. Once the desired outcome is achieved, the fixation device 150 can then be detached from the distal end 313 of the catheter shaft, and the coaptation aid 320 with coaptation catheter 321 can be safely withdrawn from the left ventricular outflow tract of the heart and from the body, and the delivery catheter 300 can be withdrawn from proximate the leaflets and from the body. If a balloon expandable scaffold is provided, it can remain in the body after the coaptation catheter is withdrawn.

As embodied herein, coaptation aid 320 can be an optional accessory for use with a delivery catheter 300 for delivering a leaflet fixation device. For example, the coaptation aid 320 can be part of a kit including a leaflet fixation device 150. Prior to a procedure, a user can observe the native anatomy and spacing between the leaflets to determine if a coaptation aid 320 will assist in the leaflet repair procedure.

The embodiments illustrated herein are adapted for repair of a heart valve and have been described in connection with repair of a mitral valve, using a leaflet fixation device delivered via an antegrade approach from a patient's left atrium and a coaptation aid delivered via a retrograde approach. However, the disclosed subject matter can be used on any other leaflet that requires intraprocedural propping or positioning to make leaflet grasping and clipping easier. For example, the disclosed subject matter could be used to position the posterior mitral leaflet, with the scaffold or balloon features adjusted to avoid interactions with the chordae tendineae or papillary muscles within the ventricle. Other exemplary leaflets include any tricuspid, aortic, or pulmonary valve leaflet, however, accessing these leaflets may require antegrade delivery of a coaptation aid. Furthermore, while shown herein as a clip, the leaflet fixation device could be any suitable fixation means, including sutures, clips, staples, and the like. In addition, while a single device was shown and described in each embodiment herein, a plurality of devices or device features can be used to simultaneously support or stabilize two or more opposing leaflets in order to further simplify the edge-to-edge repair procedure. Further, while described in connection with an edge-to-edge repair procedure, the disclosure subject matter can be adapted to aid in other procedures, such as leaflet resection, minimally invasive leaflet suturing, and chordae replacement.

While the disclosed subject matter is described herein in terms of certain embodiments for purpose of illustration and not limitation, those skilled in the art will recognize that various modifications and improvements can be made to the disclosed subject matter without departing from the scope thereof. Moreover, although individual features of the disclosed subject matter may have been discussed herein or shown in the drawings of one embodiment and not in other embodiments, it is readily apparent that individual features of one embodiment can be combined with, or substituted for, one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A kit for repair of leaflets of a heart valve, comprising:
   a coaptation aid comprising
      a coaptation catheter comprising an expandable scaffold at a distal end thereof adapted to be introduced to a left ventricular outflow tract of a heart via a retrograde approach, the expandable scaffold having a delivery configuration with a reduced cross-dimension and a deployed configuration with an expanded cross-dimension adapted to contact a ventricular side of a first leaflet of a heart valve and position the first leaflet generally proximate a coapting configuration with a second leaflet of the heart valve, and a retractable sheath having an extended position and a retracted position, the retractable sheath being adapted to retract from the extended position toward the retracted position to expose the expandable scaffold and cause the expandable scaffold to be transitioned from the delivery configuration toward the deployed configuration, the retractable sheath further adapted to extend from the retracted position to the extended position to retrieve the expandable scaffold in order to transition the expandable scaffold from the deployed configuration back to the delivery configuration; and a fixation system comprising a delivery catheter having a distal end, and a fixation device removably coupled to the distal end of the delivery catheter, the fixation device adapted to couple the first leaflet to the second leaflet of the heart valve.

2. The kit of claim 1, wherein the heart valve is a mitral valve, the first leaflet is an anterior leaflet and the second leaflet is a posterior leaflet.

3. The kit of claim 1, wherein the expandable scaffold is a self-expanding scaffold.

4. The kit of claim 3, wherein the self-expanding scaffold comprises a tapered body having a distal portion with a larger cross dimension than a proximal portion.

5. The kit of claim 3, wherein the self-expanding scaffold has a proximal end portion and a distal end portion, the distal end portion having at least one notch when in the deployed configuration to allow access of the fixation device to the first leaflet while positioned proximate the coapting configuration with the second leaflet.

6. The kit of claim 5, wherein the self-expanding scaffold has a marker proximate the at least one notch.

7. The kit of claim 1, wherein the expandable scaffold further comprises a wireless sensor.

8. The kit of claim 7, wherein the wireless sensor provides one or more representative signals selected from the group consisting of left ventricular pressure signal, cardiac output measurement signal, vessel wall motion measurement signal, and ejection fraction measurement signal.

9. The kit of claim 1, wherein the coaptation catheter is adapted for introduction via the retrograde approach through an access route selected from the group consisting of a femoral artery, a brachial artery, and a radial artery.

10. The kit of claim 1, wherein the expandable scaffold comprises a material selected from the group consisting of a metal, a super elastic material, a polymer, a bioabsorbable material and combinations thereof.

11. A method for fixation of native leaflets of a heart valve comprising:
introducing a coaptation aid comprising a coaptation catheter having an expandable scaffold at a distal end thereof to a left ventricular outflow tract of a heart via a retrograde approach, the expandable scaffold having a delivery configuration with a reduced cross-dimension and a deployed configuration with an expanded cross-dimension, the coaptation aid further comprising a retractable sheath having an extended position and a retracted position, the expandable scaffold being in the delivery configuration and the retractable sheath being in the extended position while being introduced to the left ventricular outflow tract;
retracting the retractable sheath from the extended position toward the retracted position to expose the expandable scaffold and cause the expandable scaffold to transition from the delivery configuration toward the deployed configuration to contact a ventricular side of a first leaflet of a heart valve and position the first leaflet generally proximate a coapting configuration with a second leaflet of the heart valve;
delivering a fixation device to couple the first leaflet to the second leaflet of the heart valve.

12. The method of claim 11, wherein the heart valve is a mitral valve, the first leaflet is an anterior leaflet and the second leaflet is a posterior leaflet.

13. The method of claim 11, further comprising, after delivering the fixation device,
transitioning the expandable member back to the delivery configuration;
extending the retractable sheath from the retracted position to the extended position; and
withdrawing the coaptation aid from the left ventricular outflow tract of the heart.

14. The method of claim 11, wherein the expandable scaffold is a self-expanding scaffold.

15. The method of claim 11, wherein prior to transitioning the expandable scaffold, the method further comprises aligning a distal tip of the retractable sheath proximate a hinge point of the first leaflet.

16. The method of claim 11, wherein introducing the coaptation aid includes using an access route selected from the group consisting of a femoral artery, a brachial artery, and a radial artery.

17. A method for fixation of native leaflets of a mitral valve comprising:
introducing a coaptation aid comprising a coaptation catheter having an expandable member at a distal end thereof to a left ventricular outflow tract of a heart via a retrograde approach, the expandable member having a delivery configuration with a reduced cross-dimension and a deployed configuration with an expanded cross-dimension, the expandable member in the delivery configuration while being introduced to the left ventricular outflow tract;
transitioning the expandable member from the delivery configuration toward the deployed configuration to contact a ventricular side of an anterior leaflet of the mitral valve and position the anterior leaflet generally proximate a coapting configuration with a posterior leaflet of the mitral valve; and
delivering a fixation device to couple the anterior leaflet to the posterior leaflet of the mitral valve.

18. The method of claim 17, wherein the expandable member is a balloon-expandable scaffold mounted on an expandable balloon of the coaptation catheter.

19. The method of claim 18, wherein the balloon-expandable scaffold is released in the deployed configuration from the expandable balloon at the left ventricular outflow tract.

20. The method of claim 19, wherein the balloon-expandable scaffold is made of a bioresorbable material.

21. The method of claim 19, wherein the balloon-expandable scaffold further comprises one or more beneficial agents selected from the group consisting of an anti-inflammatory agent, an anti-coagulant agent, a thrombotic agent, an oxidative stress reducing agent, a growth factor, and a pro-healing agent.

22. The method of claim 17, wherein the expandable member is a balloon.

23. The method of claim 22, wherein the balloon has a proximal end portion and a distal end portion, the distal end portion having at least one recess formed therein when in the deployed configuration to allow access of the fixation device to the anterior leaflet while positioned proximate the coapting configuration with the posterior leaflet.

24. The method of claim 23, wherein the balloon has a marker proximate the at least one recess.

25. The method of claim 22, wherein the coaptation catheter further comprises an inflation lumen in fluid communication with the balloon.

26. The method of claim 22, wherein the balloon comprises an elongate balloon.

27. The method of claim 22, wherein balloon comprises a tapered body in the deployed configuration.

28. The method of claim 27, wherein the tapered body has a distal portion with a larger cross dimension than a proximal portion.

\* \* \* \* \*